US007785638B2

(12) United States Patent
Mitra et al.

(10) Patent No.: US 7,785,638 B2
(45) Date of Patent: Aug. 31, 2010

(54) HERBAL ACNE CONTROL COMPOSITION, METHOD OF MANUFACTURING THE SAME AND USE THEREOF

(75) Inventors: Shankar Kumar Mitra, Bangalore (IN); Ekta Saxena, Bangalore (IN); Uddagiri Venkanna Babu, Bangalore (IN)

(73) Assignee: Himalaya Global Holdings, Ltd, Grand Cayman, British West Indies (KY)

( * ) Notice: Subject to any disclaimer, the term of this patent is extended or adjusted under 35 U.S.C. 154(b) by 0 days.

(21) Appl. No.: 12/180,279

(22) Filed: Jul. 25, 2008

(65) Prior Publication Data

US 2009/0220623 A1  Sep. 3, 2009

(30) Foreign Application Priority Data

Feb. 28, 2008  (IN) .......................... 478/DEL/2008

(51) Int. Cl.
*A61K 36/00* (2006.01)
*A61K 36/886* (2006.01)
*A61K 36/9066* (2006.01)

(52) U.S. Cl. ...................... 424/725; 424/744; 424/773; 424/774; 424/775; 514/846; 514/859

(58) Field of Classification Search ........................ None
See application file for complete search history.

(56) References Cited

U.S. PATENT DOCUMENTS

| 5,811,101 | A | * | 9/1998 | Waltman ..................... 424/744 |
| 5,876,737 | A | * | 3/1999 | Schonrock et al. ........... 424/401 |
| 2003/0113388 | A1 | * | 6/2003 | Phan .......................... 424/756 |
| 2007/0003582 | A1 | | 1/2007 | Heng |
| 2007/0048234 | A1 | | 3/2007 | Waugh et al. |
| 2007/0166273 | A1 | * | 7/2007 | Krivulka et al. ............... 424/74 |
| 2007/0243132 | A1 | * | 10/2007 | Russell-Jones et al. ..... 424/1.11 |

FOREIGN PATENT DOCUMENTS

WO   WO 9703674 A1 * 2/1997

OTHER PUBLICATIONS

Balbaa et al, Isolation of Salicin from Salix safsaf F. and a new TLC colorimetic method for its estimation, Egypt. J. Pharm. Sci., 20 (4): 165-173, 1979.*
Goun et al, Antibacterial and antifungal activity of Indonesian ethnomedical plants, Fitoterapia 76 (2003) 592-596.*
Pawar et al, Antibacterial activity of Aloe vera leaf gel extracts against Staphylococcus aureus, Indian Journal of Microbiology 45 (3): 227-229, 2005.*
Kusumoto et al, Screening of Some Indonesian Medicinal Plants for Inhibitory Effects of HIV-1 Protease, Shoyakugaku Zasshi, (1992) vol. 46, No. 2, pp. 190-193.*

* cited by examiner

*Primary Examiner*—Qiuwen Mi
(74) *Attorney, Agent, or Firm*—Knobbe Martens Olson & Bear LLP (57) ABSTRACT

Disclosed herein an herbal acne control compositions comprising extracts of *Swietenia mahagoni, Salix tetrasperma, Aloe vera* and *Curcuma longa* and pharmaceutically acceptable excipients. Also disclosed are the methods of making the composition, formulating the same into different delivery systems and use thereof for the prevention of acne related skin disorders in human beings.

26 Claims, 8 Drawing Sheets

Figure 12

HERBAL ACNE CONTROL COMPOSITION, METHOD OF MANUFACTURING THE SAME AND USE THEREOF

FIELD OF THE INVENTION

This invention, in general, relates to an acne control composition. More specifically, but without restriction to the particular embodiments hereinafter described in accordance with the best mode of practice, this invention provides a herbal acne control composition comprising extracts of *Salix tetrasperma, Swietenia mahagoni, Aloe Vera*, and *Curcuma longa* and method of manufacturing the same and use thereof.

BACKGROUND OF THE INVENTION

*Acne vulgaris* or acne is the most common skin disease affecting nearly 80% of persons between ages of 11 and 35 years. Acne affects all races and ethnicities with equal significance. Approximately 17 millions Americans are affected by this most common cutaneous disorder in United States.

Acne is a disease that is caused by the obstruction of sebaceous follicles, which are primarily located on the face and trunk due to excessive production of sebum in the follicles. The obstruction causes the formation of a microcomedo that may evolve into comedones such as a whitehead or a black head or an inflammatory lesion.

A blackhead occurs when the trapped sebum and bacteria partially open to the surface and turn black due to melanin, the skin's pigment. Blackheads can last for a long time because the contents very slowly drain to the surface.

The *Propionibacterium* acnes, a resident anaerobic organism, proliferate in the environment created by the mixture of excessive sebum and follicular cells and produces chemotactic factors and pro-inflammatory mediators that may lead to the inflammation.

There are many treatments available for *Acne vulgaris* depends on the type of clinical lesions. In case of comedonal acne, topical retinoids, hormonal therapies or oral isotretinoin are mostly available treatment. Benzoyl peroxide, topical antibiotics such as Clindamycin, Erythromycin, Tetracyclin and oral Isotretinoin or combination of all these medications are available for mild to moderate inflammatory acne.

To address the above problems of *Acne vulgaris*, major research activities have been directed towards developing a acne control composition that can effective against the four processes of Acne viz. sebum production, hyperkeratinization, infection with *propionibacterium* acnes and inflammation. The present invention is an outcome of years of research to identify an herbal remedy possess anti inflammatory, anti kerolytic, sebum control and anti bacterial agent and methods of developing the same as cosmeceutical product for topical application for control and treatment of *Acne vulgaris*.

PRIOR ART

United States Patent Application No. 20070003582 by Heng et al. teaches the preparation of topical medication comprises curcumin, water, alcohol, cellulose, carbomer, diazolinyl urea and anti inflammatory agent and other excipients for treatment of acne and for reversing of ageing and sun damage.

United States Patent Application No. 20070048234 by Waugh et al. teaches the preparation of anti acne kit comprises vasoconstrictor, anti acne agent, skin cleanser, an astringent and a sunscreen for treating severe cases of acne.

SUMMARY OF THE INVENTION

It is a principal object of the present invention to provide an herbal acne control composition comprising extracts of *Salix tetrasperma, Swietenia mahagoni, Aloe vera*, and *Curcuma longa* and pharmaceutically acceptable excipients.

Another object of the present invention is to provide an herbal acne control composition comprises extracts of *Salix tetrasperma, Swietenia mahagoni, Aloe vera*, and *Curcuma longa*, wherein said composition is also effective for any other skin related disorder.

Another object of the present invention is to provide a process for preparing herbal acne control composition comprising extracts of *Salix tetrasperma, Swietenia mahagoni, Aloe vera*, and *Curcuma longa*, wherein the process provides selection of solvents to obtain extracts of said herbs having rich bioactive constituents.

Yet another object of the present invention is to provide an acne control composition, wherein said composition is effective for anti inflammatory, anti bacterial, anti kerolytic and anti-seborrhatic activities.

The above and the other objects of the present invention are attend according to following preferred embodiments of the present invention, however the scope of the invention is not restricted to the particular embodiment.

In accordance with one preferred embodiment of the present invention, there is provided a herbal acne control composition, wherein the composition comprising the extracts of *Aloe vera, Salix tetrasperma, Swietenia mahagoni* and *Curcuma longa* and pharmaceutically acceptable excipients selected from binder, diluent, surfactant, perfume and preservative as a carrier or otherwise.

In accordance with another preferred embodiment of the present invention, there is provided a herbal acne control composition, wherein the extract is obtained from all or any specific part/s of said herbs, preferably leaves of *Aloe vera*, bark of *Swietenia mahagoni* and *Salix tetrasperma* and rhizomes of *Curcuma longa*.

In yet another preferred embodiment, there is provided a process for preparation of herbal acne control composition, wherein, the process comprises of extracting the bark of *Salix tetrasperma* employing any suitable extraction technique, preferably a hot-soxhlation or percolation technique and wherein a selective solvent or solvent system are used to yield high extractive value and rich content of stable bioactive salicylic acid. Said solvent is selected from a group of organic solvents and water, preferably non polar long chain hydrocarbon, an ester, most preferably selected from n-hexane, diethyl ether, dichloromethane, chloroform, ethyl acetate, acetone, methanol, ethanol alone or in combination thereof.

In accordance with another preferred embodiment of the present invention, there is provided a method for extraction of bark of *Swietenia mahagoni*, wherein said extraction method is performed using any suitable extraction technique, preferably a hot-soxhlation or percolation technique and wherein a selective solvent or solvent system are used to yield high extractive value and rich content of stable bioactive ingredients. Said solvent is selected from a group of organic solvents and water, preferably lower chain alcohol/s and water, most preferably water.

In accordance with another embodiment of the present invention, there is provided a method for extraction of leaves of *Aloe vera*, wherein said extraction method is performed using any suitable extraction technique, preferably a hot-soxhlation or percolation technique and wherein a selective solvent or solvent system are used to yield high extractive value and rich content of stable bioactive ingredients including but are not limited to mono and di saccharides. Said solvent is selected from a group of organic solvents and water, preferably lower chain alcohol/s and water, most preferably methanol.

In accordance with another embodiment of the present invention, there is provided a method for extraction of rhizomes of *Curcuma longa*, wherein said extraction method is performed using any suitable extraction technique, preferably a hot-soxhlation or percolation technique and wherein a selective solvent or solvent system are used to yield high extractive value and rich content of stable bioactive ingredients including but are not limited to tetrahydrocurcuminoids. Said solvent is selected from a group of organic solvents and water, preferably halo hydrocarbons and lower chain alcohol, most preferably selected from dichloromethane and methanol alone or in combination thereof.

In still another preferred embodiment of the present invention, there is provided a process for preparation of acne control composition, wherein, the process comprises of extracting the herbs by percolation method employing suitable solvent, filtering the resultant herbs extract, concentrating the extract to dryness on a rotatory evaporator or on a steam bath at optimum temperature and producing a herbal composition comprising the said dry extract and pharmaceutically acceptable excipients.

In still another preferred embodiment of the present invention, there is provided a process for preparation of acne control composition, wherein, the process comprises of extracting the herbs by hot-soxhlation method employing suitable solvent, filtering the plant extract, concentrating the plant extract to dryness on a rotatory evaporator or on a steam bath at optimum temperature and producing a herbal composition comprising the said dry extract and pharmaceutically acceptable excipients.

In accordance with another preferred embodiment of the present invention, there is provided a method of screening of *Swietenia mahagoni* water extract for antibacterial activity against *Propionibacterium* acnes.

In accordance with another embodiment of the present invention, there is provided a herbal acne control composition, wherein said composition is formulated in various delivery system preferably in the form of cream, face wash, face gel, face scrub or face pack.

BRIEF DESCRIPTION OF THE FIGURES

Further objects of the present invention together with additional features contributing thereto and advantages accruing there from will be apparent from the following description of preferred embodiments of the invention which are shown in the accompanying drawings and figures, wherein:

FIG. 4-11. Representative photomicrographs of Rabbit ear skin obtained from different groups (Histopathology)

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention discloses an herbal acne control composition, wherein the composition comprising the extracts of *Aloe vera, Salix tetrasperma, Swietenia mahagoni* and *Curcuma longa* and pharmaceutically acceptable excipients selected from but are not limited to binder, diluent, surfactant, perfume and preservative as a carrier or otherwise.

The disclosed acne control composition is effectively used for the any skin related problem, preferably acne control. Said composition provides protection to the user from mild to severe pimples, black heads, white heads, papules, nodules, pustules, inflammatory lesions and cysts and free from any toxicity, toxic residues and irritation if used.

The herbs extracts according to the present invention are screened to characterize the therapeutic effectivity, such as for anti-inflammatory activity of *Curcuma longa* extract, anti-seborrhatic activity of *Aloe vera* extract, anti-bacterial activity of *Swietenia mahagoni* and anti-kerolytic activity of *Salix tetrasperma*.

The solvent extract of *Salix tetrasperma* is standardized against salicylic acid by High Performance Liquid Chromatography technique. In the same line, extracts of *Aloe vera, Curcuma longa*, and *Swietenia mahagoni* are also standardized employing their respective phytochemical marker such as carbohydrates and curcuminoids respectively.

The present invention involves the selection and identification of the herbs and obtaining the extract by subjecting the same to solvent extraction. The bioassay guided fractionation of extracts to identify the active compounds and to develop a herbal composition comprising extracts and fractions of *Aloe vera, Curcuma longa, Salix tetrasperma, Swietenia mahagoni* and a safe cosmeceutical composition for treatment and control of Acne and other skin related diseases in human beings.

The examples that follow are not intended to limit the scope of the invention as defined hereinabove or as claimed below.

EXAMPLE 1

Preparation of Extract from the Leaves of *Aloe vera* by Percolation Method

The shade dried material of leaves of *Aloe vera* is pulverized to coarse powder and about 1 Kg each of powdered material placed in different flasks and extracted with n-hexane, diethyl ether, dichloromethane, chloroform, ethyl acetate, acetone, methanol, ethanol and water at room temperature for 24 h to 48 h., then plant extracts were filtered and concentrated to dryness on rotatory evaporator or on steam bath at optimum temperature and under reduced pressure.

EXAMPLE 2

Preparation of Extract from the Leaves of *Aloe vera* by Hot-soxlation Method

The coarse powdered material of leaves of *Aloe vera* is subjected to hot-soxhalation using solvents n-hexane, diethyl ether, dichloromethane, chloroform, ethyl acetate, acetone, methanol, ethanol and water at optimum temperature and recycled until extraction is completed, then plant extracts were filtered and concentrated to dryness on rotatory evaporator or on steam bath at optimum temperature. All the above described respective solvent extracts manufactured by percolation and hot-soxhalation methods are qualitatively similar to each other.

EXAMPLE 3

Preparation of Extract from the Bark of *Salix tetrasperma* by Percolation Method The shade dried material of bark of *Salix tetrasperma* is pulverized to coarse powder and about 1 Kg each of powdered material placed in different flasks and extracted with n-hexane, diethyl ether, dichloromethane, chloroform, ethyl acetate, acetone, methanol, ethanol, water, n-hexane:chloroform (1:1), n-hexane:ethyl acetate (1:1), n-hexane:acetone (1:1), chloroform:acetone (1:1), ethyl acetate:methanol (1:1), acetone:water (1:1) and methanol:water (1:1) at room temperature for 24 h to 48 h., then plant extracts were filtered and concentrated to dryness on rotatory evaporator or on steam bath at optimum temperature and under reduced pressure.

EXAMPLE 4

Preparation of Extract from the Bark of *Salix tetrasperma* by Hot-soxlation Method The coarse powdered material of bark of *Salix tetrasperma* is subjected to hot-soxhalation using solvents n-hexane, diethyl ether, dichloromethane, chloroform, ethyl acetate, acetone, methanol, ethanol, water, n-hexane:chloroform (1:1), n-hexane:ethyl acetate (1:1), n-hexane:acetone (1:1), chloroform:acetone (1:1), ethyl acetate:methanol (1:1), acetone:water (1:1) and methanol:water (1:1) at optimum temperature and recycled until extraction is completed, then plant extracts were filtered and concentrated to dryness on rotatory evaporator or on steam bath at optimum temperature. All the above described respective solvent extracts manufactured by percolation and hot-soxhalation methods are qualitatively similar to each other. The yield of each extract is summarized in table-1.

TABLE 1

| S. No | Code No. | Mode of extraction | Yield (%) | Nature of extract |
|---|---|---|---|---|
| 1 | ERS-1 | Hexane | 1.00 | Green colour sticky |
| 2 | ERS-2 | Solvent ether | 1.50 | Green colour sticky |
| 3 | ERS-3 | Chloroform | 2.00 | Green colour sticky |
| 4 | ERS-4 | Dichloromethane | 2.20 | Green colour sticky |
| 5 | ERS-5 | Hexane:chloroform(1:1) | 0.90 | Green colour sticky |
| 6 | ERS-6 | Ethylacetate | 1.80 | Green colour sticky |
| 7 | ERS-7 | Methanol | 6.00 | Brown powder |
| 8 | ERS-8 | Ethylalcohol | 5.50 | Brown powder |
| 9 | ERS-9 | Hexane:ethylacetate (1:1) | 2.00 | Green colour sticky |
| 10 | ERS-10 | Hexane:Acetone(1:1) | 1.80 | Green colour sticky |
| 11 | ERS-11 | Chloroform:acetone (1:1) | 2.00 | Green colour sticky |
| 12 | ERS-12 | Acetone | 3.00 | Brown powder |
| 13 | ERS-13 | Ethylacetate:methanol (1:1) | 5.00 | Brown powder |
| 14 | ERS-14 | Acetone:water (1:1) | 15.00 | Brown powder |
| 15 | ERS-15 | Methanol:water (1:1) | 10.00 | Brown powder |
| 16 | ERS-16 | Water | 6.00 | Brown powder |

EXAMPLE 5

Preparation of Extract from the Bark of *Swietenia mahagoni* by Percolation Method The shade dried material of bark of *Swietenia mahagoni* is pulverized to coarse powder and about 1 Kg each of powdered material placed in different flasks and extracted with n-hexane, diethyl ether, dichloromethane, chloroform, ethyl acetate, acetone, methanol, ethanol and water at room temperature for 24 h to 48 h, then plant extracts were filtered and concentrated to dryness on rotatory evaporator or on steam bath at optimum temperature and under reduced pressure.

EXAMPLE 6

Preparation of Extract from the Bark of *Swietenia mahagoni* by Hot-soxlation Method The coarse powdered material of bark of *Swietenia mahagoni* is subjected to hot-soxhalation using solvents n-hexane, diethyl ether, dichloromethane, chloroform, ethyl acetate, acetone, methanol, ethanol and water at optimum temperature and recycled until extraction is completed, then plant extracts were filtered and concentrated to dryness on rotatory evaporator or on steam bath at optimum temperature. All the above corresponding solvent extracts manufactured by percolation and hot-soxhalation methods are qualitatively similar to each other.

EXAMPLE 7

Preparation of Extract from the Rhizomes of *Curcuma longa* by Percolation Method The shade dried material of rhizomes of *Curcuma longa* is pulverized to coarse powder and about 1 Kg each of powdered material placed in different flasks and extracted with n-hexane, diethyl ether, dichloromethane, chloroform, ethyl acetate, acetone, methanol, ethanol and water at room temperature for 24 h to 48 h., then plant extracts were filtered and concentrated to dryness on rotatory evaporator or on steam bath at optimum temperature and under reduced pressure.

EXAMPLE 8

Preparation of Extract from the Rhizomes of *Curcuma longa* by Hot-soxlation Method The coarse powdered material of rhizomes of *Curcuma longa* is subjected to hot-soxhalation using solvents n-hexane, diethyl ether, dichloromethane, chloroform, ethyl acetate, acetone, methanol, ethanol and water at optimum temperature and recycled until extraction is completed, then plant extracts were filtered and concentrated to dryness on rotatory evaporator or on steam bath at optimum temperature. All the above corresponding solvent extracts manufactured by percolation and hot-soxhalation methods are qualitatively similar to each other.

EXAMPLE 9

Standardization of Methanolic Extract of *Aloe vera* by HPLC

Sample preparation: Accurately 100 mg of methanolic extract was weighed in 100 ml of volumetric flask and dissolved in Water:Methanol (1:1) solvent mixture and made upto the volume of 100 ml to get 1 mg/ml concentration.

Figure 1:
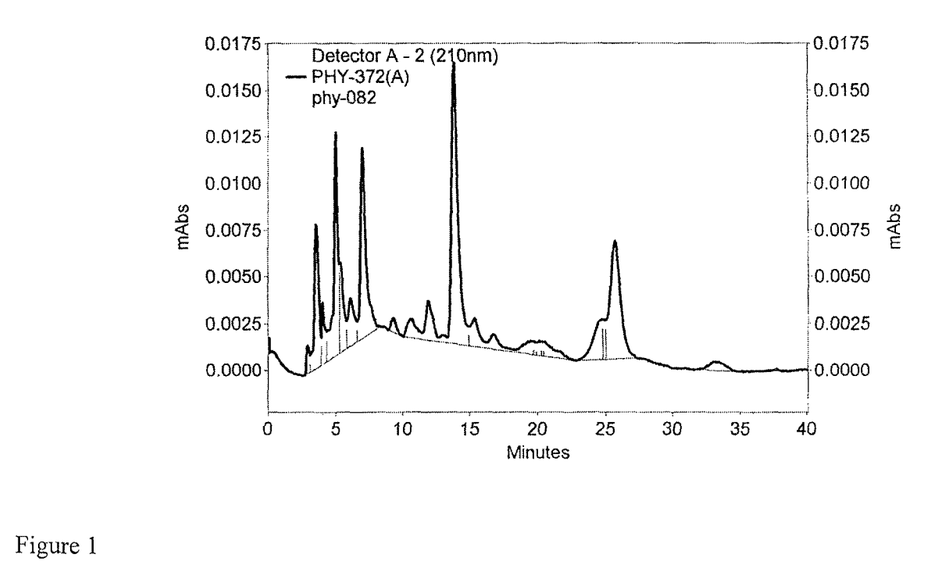
FIG. 1. HPLC chromatogram of methanolic extract of *Aloe vera*

HPLC conditions: Accurately 20 uL of the sample was injected over reverse phase column and run with mobile phase of 0.1% of Phosphoric acid and water in the ratio of 90:10 at flow rate of 1 ml/min. and detected at 210 nm. The chromatogram of the same is given as FIG. 1.

EXAMPLE-10

Standardization of Extracts of *Salix tetrasperma* by HPLC

Standard preparation: Accurately weighed 10 mg of Salicylic acid is taken into 10 ml of volumetric flask and dissolved in HPLC grade methanol and sonicate for 5 min. This standard solution is further diluted with methanol to get 100 ug/ml as working standard.

Sample preparation: Accurately 100 mg of each extract was weighed in 100 ml of volumetric flask and dissolved in HPLC grade methanol and made upto the volume of 100 ml to get 1 mg/ml concentration.

HPLC conditions: Accurately 20 uL of the sample is injected over reverse phase column and run with mobile phase of 0.1% acetic acid in water and methanol in the ratio of 60:40 at flow rate of 1 ml/min and detected at 270 and 254 nm.

Figure 2:
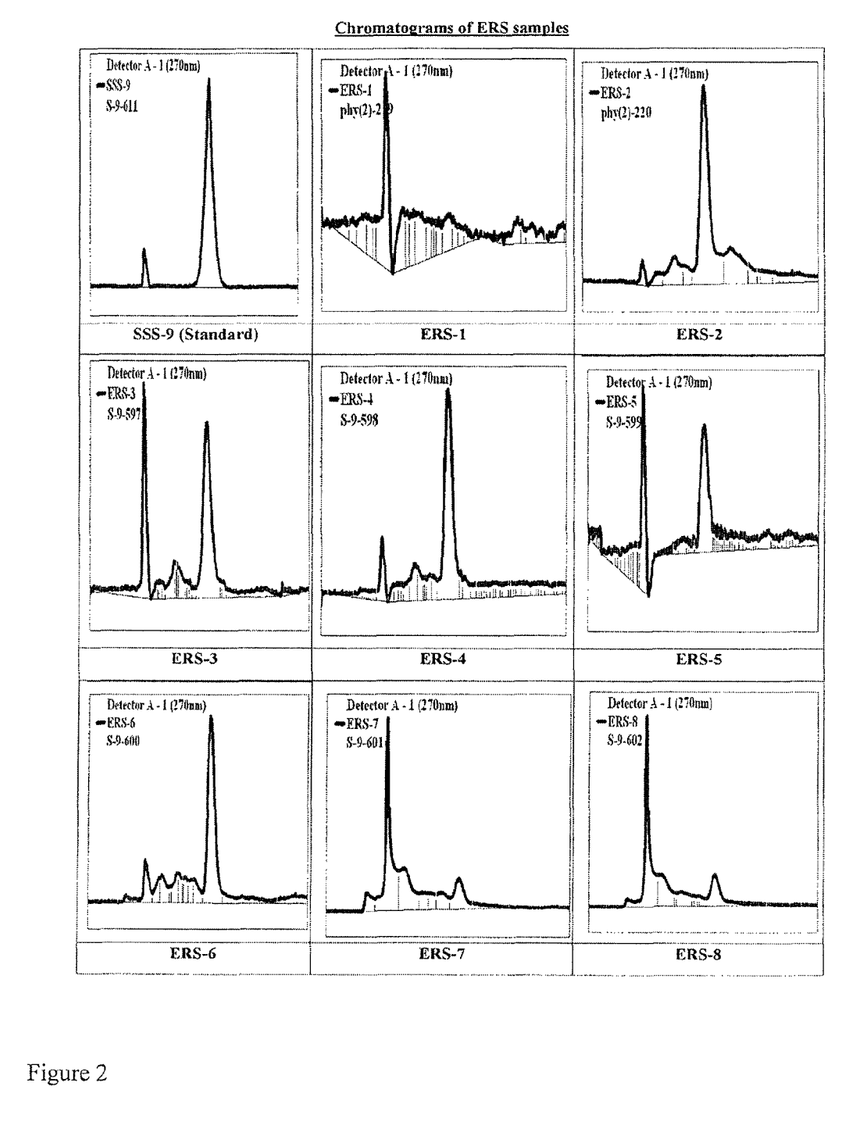
FIG. 2. HPLC chromatograms of solvent extracts of *Salix tetrasperma*

The chromatogram of each extract is given in FIG. 2 and percentage composition of salicylic acid is given in table.2.

TABLE 2

| S. No. | Code No | Yield (%) of Salicylic acid |
|---|---|---|
| 1 | ERS-1 | Not detected |
| 2 | ERS-2 | 6.48 |
| 3 | ERS-3 | 1.98 |
| 4 | ERS-4 | 2.48 |
| 5 | ERS-5 | 0.58 |
| 6 | ERS-6 | 4.40 |
| 7 | ERS-7 | 4.53 |
| 8 | ERS-8 | 4.34 |
| 9 | ERS-9 | 7.54 |
| 10 | ERS-10 | 8.91 |
| 11 | ERS-11 | 6.44 |
| 12 | ERS-12 | 4.62 |
| 13 | ERS-13 | 5.40 |
| 14 | ERS-14 | 2.66 |
| 15 | ERS-15 | 2.79 |
| 16 | ERS-16 | 0.74 |

EXAMPLE-11

Fractionation and Column Chromatography of Water Extract of *Swietenia mahagoni*

About 400 g of the water extract is fractionated into methanol soluble fraction and methanol insoluble fractions. The yield of the methanol soluble fraction is 48%. The methanol soluble fraction is subjected to column chromatography using silica gel as adsorbent and eluted in the column with n-hexane, ethyl acetate and methanol. The details are given in Table. 3.

TABLE 3

| S. No | Fraction No | Solvent used for elution | Yield | | Nature of fractions |
|---|---|---|---|---|---|
| 1 | AV-32/2 | Hexane | 100 | mg | Colourless oily |
| 2 | AV-32/3 | Hexane:ethylacetate(95:5) | 100 | mg | Colourless oily |
| 3 | AV-32/4 | Hexane:ethylacetate(90:10) | 350 | mg | Yellow oily |
| 4 | AV-32/5 | Hexane:ethylacetate(85:15) | 200 | mg | Yellow waxy |
| 5 | AV-32/6 | Hexane:ethylacetate(80:20) | 500 | mg | Yellow waxy |
| 6 | AV-32/7 | Hexane:ethylacetate(75:25) | 250 | mg | Brown oily |
| 7 | AV-32/8 | Hexane:ethylacetate(70:30) | 200 | mg | Brown oily |
| 8 | AV-32/9 | Hexane:ethylacetate(60:40) | 230 | mg | Light brown syrupy |
| 9 | AV-32/10 | Hexane:ethylacetate(50:50) | 300 | mg | Light brown syrupy |
| 10 | AV-32/11 | Hexane:ethylacetate(25:75) | 400 | mg | Light brown syrupy |
| 11 | AV-32/12 | Ethylacetate | 18 | g | brown syrupy |
| 12 | AV-32/13 | Ethylacetate:methanol (95:5) | | | |
| 13 | AV-32/14 | Ethylacetate:methanol (90:10) | | | |
| 14 | AV-32/15 | Ethylacetate:methanol (85:15) | 2 | g | Dark brown syrupy |
| 15 | AV-32/16 | Ethylacetate:methanol (80:20) | 1 | g | Dark brown syrupy |
| 16 | AV-32/17 | Ethylacetate:methanol (70:30) | 2 | g | Dark brown syrupy |
| 17 | AV-32/18 | Ethylacetate:methanol (60:40) | 1.3 | g | Dark brown syrupy |
| 18 | AV-32/19 | Ethylacetate:methanol (50:50) | 1.0 | g | Brown syrupy |
| 19 | AV-32/20 | Ethylacetate:methanol (25:75) | 2.5 | g | Brown syrupy |
| 20 | AV-32/21 | Methanol | 51 | g | Dark brown pasty |

EXAMPLE-12

Standardization of *S. Mahagoni* Water Extract by HPLC

Sample preparation: The water extract (AV-32) is accurately weighed for 100 mg in volumetric flask, dissolved in water and sonicated for 5 minutes to make up the volume to 100 ml to get the concentration of 1 mg/ml sample solution and filtered through 0.2 micron syringe filter.

Mobile Phase Preparation: Accurately 1.88 g of Hexane Sulfonic Acid Sodium salt is added to 10 ml of glacial Acetic acid and 1.3 ml of Triethylamine in 1 L volumetric flask and volume is made upto the mark with double distilled water. The mobile phase is sonicated for 10 minutes and filtered through 0.45 u filter paper.

Figure 3:
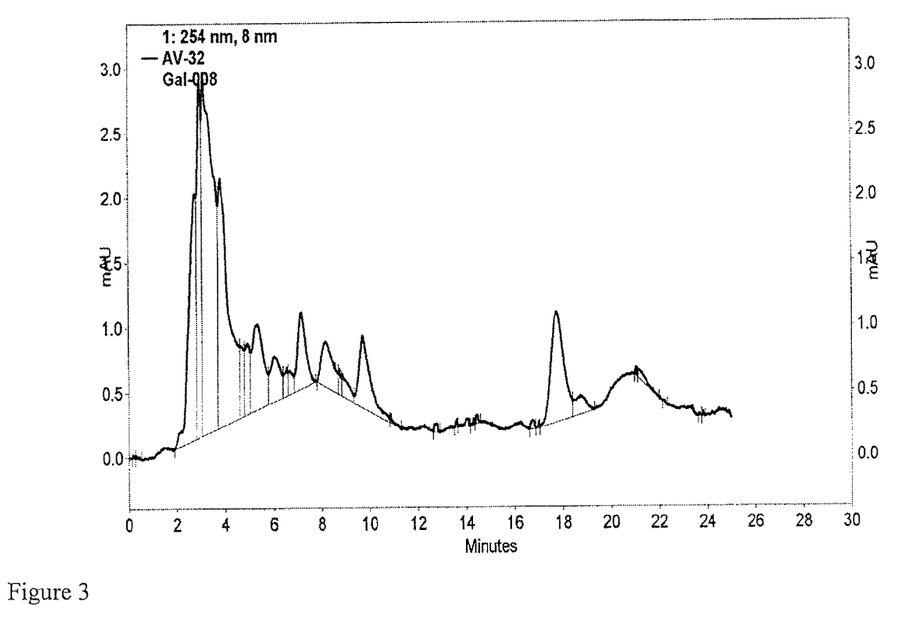
FIG. 3. HPLC chromatogram of water extract of *Swietenia mahagoni*
Figure 4:
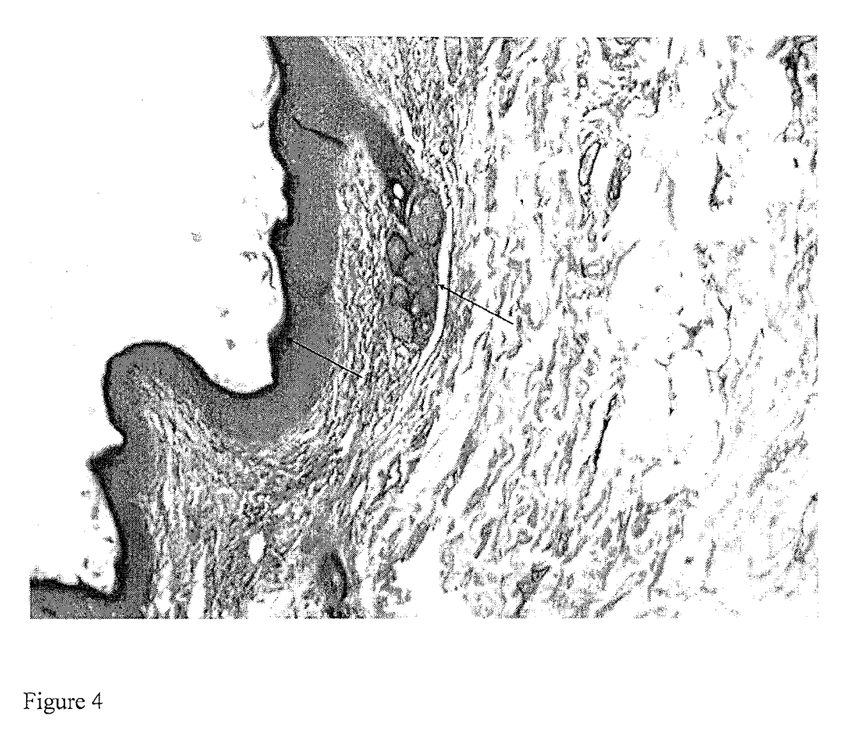
FIGS. 4. & 5. Shows normal skin architecture of rabbit car (Group-1)
Figure 5:
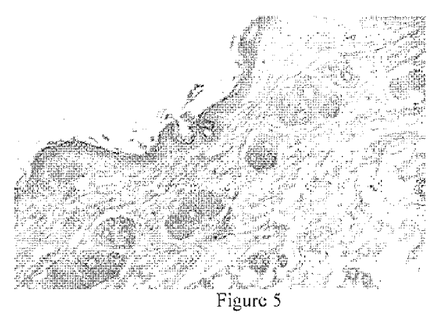
Figure 6:
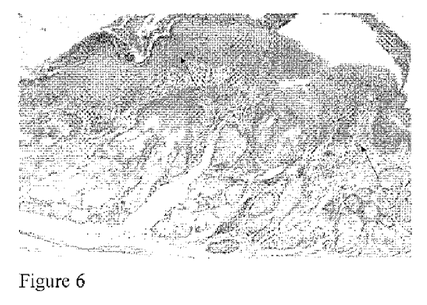
FIGS. 6. & 7. Showing intense epithelial and sebaceous gland proliferation and also infiltration of Inflammatory cells in untreated positive control (Group-2). The changes are indicated by arrows.
Figure 7:
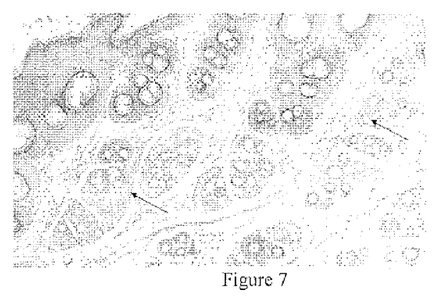
Figure 8:
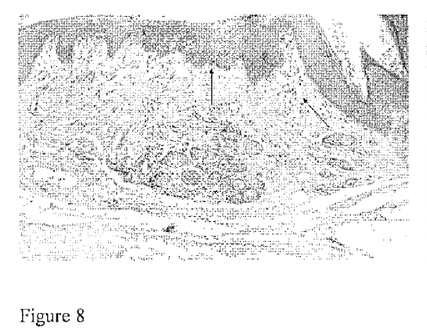
FIGS. 8. & 9. Showing reversal of epithelial and sebaceous gland proliferation and also infiltration of inflammatory cells in Tretenoin (0.025%) cream treatment group (Group-3)
Figure 9:
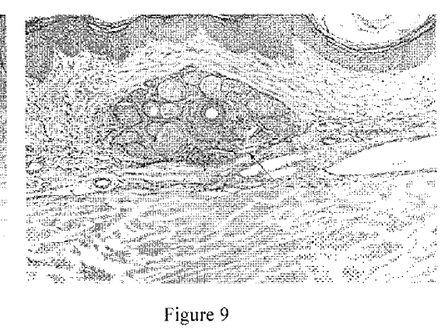
Figure 10:
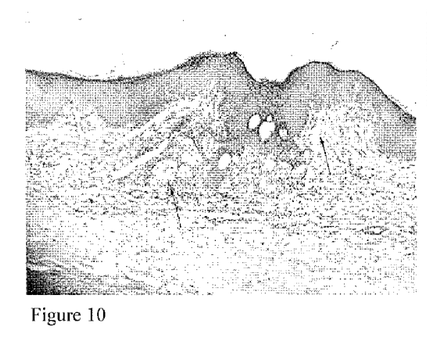
FIGS. 10. & 11. Showing higher degree of reversal of epithelial and sebaceous gland proliferation and also infiltration of inflammatory cells in FD/OCC/10 cream application group (Group-4)
Figure 11:
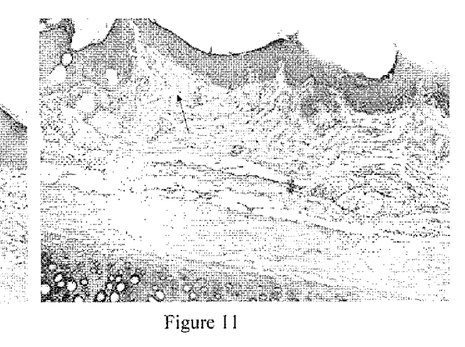

HPLC conditions: Accurately 20 uL of samples is injected over reverse phase column and ran with the mobile phase at 1 ml/min and detected at 254 nm. HPLC chromatograms are summarized in FIG. 3.

EXAMPLE-13

Antibacterial Activity of Extracts of S. mahagoni Against Propionibacterium Acnes Plant Extract Preparation: The stock solutions of the plant extracts are prepared in Dimethyl Sulphoxide (DMSO) or in double distilled water as per the solvent specifications. The working solution (100 mg/ml) is prepared accordingly.

Bacterial strains—Propionibacterium acnes: The bacterial strain (MTCC No. 1951) is procured from Microbial Type Culture Collection Chandigarh. The strain is re-cultured, maintained in Rabbit Blood Agar plates (Blood Agar with 5% Sterile rabbit blood) as well as Fluid Thioglycollate medium. The cultures are stained by Grams staining procedure and are observed for their characteristics.

In-vitro Anti-bacterial Activity Evaluation

Anti-bacterial activity is evaluated by Agar well diffusion assay & by Minimal Inhibitory concentration (MIC) evaluation.

Agar Well Diffusion Assay

The Rabbit Blood Agar plates are inoculated with the broth culture of (Density equivalent to $1/100^{th}$ dilution of 0.5 McFarland turbidometer) P. acnes with a sterile cotton swab. 6 mm wells are punched on the agar and filled with the plant extract (100 mg/ml). Plates are kept in anaerobic jar incubated in incubator set at 37° C. for 48 hrs. Zones of inhibition are measured & recorded in millimetre (mm).

Minimal Inhibitor Concentration (MIC) Evaluation

The Rabbit Blood Agar is prepared & kept molten at 55° C. Different dilution of plant extracts & solvents are taken in a sterile 50 mm petriplates. The extracts are diluted with molten agar to make up the volume to 4 ml. After solidification of the media, the plates are inoculated with 20 µl of broth culture of (Density equivalent to $1/100^{th}$ dilution of 0.5 McFarland turbidometer) P. acnes. Plates are incubated for 48 hrs at 37° C. MIC is determined as the minimum concentration of the drug showing maximum inhibition. Results are recorded in Table-4.

TABLE 4

| Organism Tested | Extract | Zone of Inhibition | MIC |
| --- | --- | --- | --- |
| P. acnes | S. Mahagoni water extract | 31 mm | 2 mg |
|  | S. Mahagoni methanol extract | 34 mm | 4 mg |

EXAMPLE-14

Comparative Evaluation of Aloe vera Extracts with Tretenoin for Anti-seborrhatic Activity in Rabbits Material and Methods: Laboratory bred New Zealand white rabbits weighing between 2.2-2.7 kgs were used for the study. The animals were housed and acclimatised to a constant temperature of 22±2° C. and will be exposed to 12 hrs day & night cycle. The animals were fed with synthetic diet and water ad libitum.

Procedure: Twenty-four rabbits were divided into 4 groups of six each. UV irradiated oleic acid is applied to the ventral surface of the rabbit ears, near the auditory canal, using camlin brush for 28 days. Group I rabbits did not receive the comedogen and serves as control. Rabbits from group II were applied with comedogen (UV irradiated oleic acid) for 28 days and served as positive control. Rabbits from group III and IV were applied with comedogen. After two hours of the comedogen application anti-acne creams Tretenoin and plant extracts were applied respectively for 28 days. Ear tissue was collected on $28^{th}$ day for histopathological evaluation. The tissues were fixed in 10% neutral buffered formalin (NBF), the formalin fixed tissues were then processed by paraffin technique, and sections of 5-µm thickness cut and stained by the routine H & E method. The histopathological changes were recorded semi-quantitatively by an experienced and qualified histopathologist.

Group Classification:

| Group | No. of animals | Treatment |
| --- | --- | --- |
| 1 | 6 | Normal control |
| 2 | 6 | Positive control (oleic acid application alone) |
| 3 | 6 | Oleic acid + Tretenoin (0.025%) Cream |
| 4 | 6 | Oleic acid + Aloe vera extract |

UVA irradiation of Oleic acid: Oleic acid is poured into a glass petriplates to form a thin layer and exposed to UVA irradiation from 300 W sun lamp for 18 hrs.

Results: Summary of lesions observed in all groups is given in table-5 and histopathological pictures are shown in FIGS. 4-11.

TABLE 5

|  |  | Groups | | | |
| --- | --- | --- | --- | --- | --- |
| Lesions | Intensity | 1 (n = 6) | 2 (n = 6) | 3 (n = 6) | 4 (n = 6) |
| Epithelial proliferation | ++ | 0 | 0 | 0 | 100 |
|  | +++ | 0 | 0 | 100 | 0 |
|  | ++++ | 0 | 100 | 0 | 0 |
| Sebaceous glandular proliferation | + | 0 | 0 | 0 | 50 |
|  | ++ | 0 | 0 | 50 | 50 |
|  | ++++ | 0 | 100 | 50 | 0 |
| Inflammatory cell collection | +++ | 0 | 50 | 50 | 100 |
|  | ++++ | 0 | 50 | 50 | 0 |

EXAMPLE-15

Screening of Plant Extracts for Topical Anti-inflammatory Activity Using Croton Oil Induced Model of Ear Edema in Rats The objective of this study is to evaluate the topical anti-inflammatory properties of Tetrahydrocurcuminoids (THC-09) and Curcuminoids from *Curcuma longa* extract (CU-18) by croton oil induced ear edema model in rats and compare its activity against standard reference drugs Hydrocortisone and Diclofenac.

Animals: Around 40 male rats of Wistar strain weighing between 150 to 200 gms were used for the study. The animals were procured from in-house animal house and quarantined for 7 days before the start of the experiment and subjected for routine veterinary examination. Local animal ethics committee approved the protocol of the study. Animals were housed under standard laboratory conditions, air-conditioned with adequate fresh air supply (12-15 air changes/hr). Environment: temperature 19-25° C., relative humidity 30-70%, with a 12 hr light and 12 hr dark cycle. Temperature and humidity were recorded.

Animals were housed in groups of 4 per cage in standard polypropylene cages (size approximately: L 410×B 220× H140 mm), with stainless steel top grill having facilities for pelleted food and drinking water in bottle; bedding: steam sterilized clean paddy husk was used and changed at least thrice a week. Rats/Mice (pellet) Feed manufactured by M/s. Tetragon Chemie Pvt. Ltd., Bangalore, India were provided. Deep bore-well water passed through activated charcoal filter and exposed to UV rays in Aqua guard on-line water filter-cum-purifier manufactured by Eureka Forbes Ltd., Mumbai, India was provided.

Based on the body weight stratification rats were randomized into 5 groups of 8 animals each, and each animal was coded and identified by their unique accession number.

Chemicals and Reagents

All the chemicals and reagents used were of analytical grade.

Croton Oil Preparation:

4 parts croton oil, 10 parts ethanol, 20 parts pyridine, 66 parts ethyl ether 200 µl croton oil, 500 µl ethanol,1000 µl pyridine, 3300 µl ethyl ether and 5000 µl of the total mixture will be kept in 5 aliquots of 1 ml each and this mixture was stored in a place away from light. The test compounds were solubilized in this preparation just before the topical application.

Test Compounds and Concentration:
1. THC-09 (Tetrahydrocurcuminoids), 10 mg/ml of croton oil preparation.
2. CU-18 (*Curcuma longa* extract), 10 mg/ml of croton oil preparation.
3. Hydrocortisone, 1 mg/ml of croton oil preparation.
4. Diclofenac, 2 mg/ml of croton oil preparation.

Procedure:

For testing in rats the above-mentioned croton oil mixture was prepared in aliquots of 1 ml just before use. The reference and the test compounds were also dissolved in the same solution. The animals were divided in to 5 groups of 8 animals each. Group-I animals received 20 µl of croton oil preparation topically on both sides (inner and outer surface) of left ear for induction of inflammation. Group-II, III, IV and V animals were treated with THC-09, CU-18, Hydrocortisone and Diclofenac (all solubilized in croton oil preparation) in a similar manner as that of group I respectively, the concentration of drugs was as described above.

The animals were observed for erythema and edema of the ear and thickness of same was measured after second and third hour after the croton oil application. A visual scoring was also recorded unequivivocally by two independent observers. The scoring pattern is as follows; Low=1, Medium=2, and High=3, on the basis of erythema and thickness of the ear compare to right normal ear.

Statistics: All the data were analyzed by one-way ANOVA followed by Dunnet's post multiple comparison test.

Figure 12:
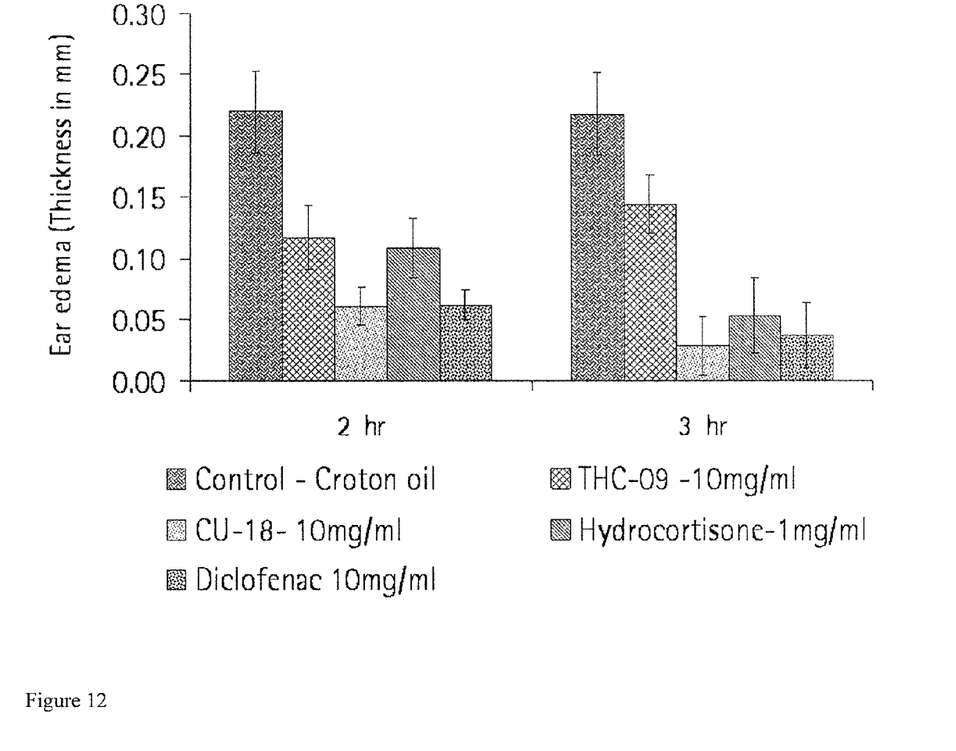
FIG. 12. Topical anti-inflammatory activity of Tetrahydro curcuminoids (THC-09) and *Curcuma longa* extract (CU-18) in Croton oil induced ear edema.

Result: It was found that, the application of croton oil preparation to rat ear's, greatly increased the erythema and edema coupled with increase in thickness of ear. All the tested drugs significantly reversed these changes, when tested in above mentioned manner and dose in both 2 and 3-hour post administration. Results are summarized in FIG. 12.

EXAMPLE-16

Manufacturing Process of Acne Control Face Cream

TABLE 6

| Phase | Name of the Ingredients | % Use |
|---|---|---|
| A | Octyl Stearate | 2.00 |
|   | Capric/Caprylic Triglyceride | 2.00 |
|   | Steareth 2 | 2.0 |
|   | Steareth 21 | 1.5 |
|   | Cetostearyl alcohol | 1.5 |
|   | Stearic Acid | 2.0 |
|   | Cetyl Palmitate | 1.0 |
|   | Propyl Paraben | 0.1 |
|   | Extract of *Salix tetrasperma* | 0.1 |
|   | DC-200 | 0.5 |
| B | DM Water | Qs |
|   | Glycerine | 2.0 |
|   | Xanthan Gum | 0.2 |
|   | Acrylates/C10-30 alkyl acrylate Crosspolymer | 0.2 |
|   | Di Sodium EDTA | 0.05 |
|   | Extract of *Aloe vera* | 0.2 |
|   | Extract of *Swietenia mahagoni* | 0.2 |
|   | Extract of *Curcuma longa* | 0.1 |
|   | Propylene Glycol | 5.0 |
|   | Methyl paraben | 0.2 |
| C | Phenoxy ethanol | 0.3 |
|   | Vit E Acetate | 0.2 |
| D | Perfume | Qs |

Manufacturing Procedure
1. Heat Phase A to 80° C.
2. Dissolve Di sodium EDTA in Water. Disperse Gum and polymer in water. Dissolve active in the water phase. Add all the remaining ingredients in the phase. Heat to 80° C.
3. Add Phase A into Phase B at 80° C. Mix for 15 min.
4. Start Cooling
5. Add Phase C at 50° C., mix well
6. Add Phase D at 45° C., mix well

EXAMPLE-17

Manufacturing Process of Acne Control Face Wash

TABLE 7

| S. No. | Ingredients | % Ingredients |
|---|---|---|
| 1. | Extract of *Aloe vera* | 0.05 |
| 2. | Extract of *Swietenia mahagoni* | 0.05 |

TABLE 7-continued

| S. No. | Ingredients | % Ingredients |
|---|---|---|
| 3. | Extract of *Salix tetrasperma* | 0.10 |
| 4. | Extract of *Curcuma longa* | 0.10 |
| 5. | Glycolic acid | 0.55 |
| 6. | Disodium EDTA | 0.05 |
| 7. | PEG-7 glyceryl cococate | 2.00 |
| 8. | Plantacare 818 UP (Coco glucoside) | 30.00 |
| 9. | Plantacare 2000 UP (Coco glucoside) | 15.00 |
| 10. | Amaze XT (Dehydro xanthangum) | 1.50 |
| 11. | Glycacil 2000 (IPBC) | 0.30 |
| 12. | Neolone PE (MIC & Phenoxyethanol) | 0.60 |
| 13. | Perfume | 0.40 |
| 14. | DM Water | 49.30 |
| 15. | Total | 100.00 |

Manufacturing Method

The two-plantacare ingredients Plantacare 818 UP and Plantacare 2000 UP are weighed in main vessel as per formula and its pH is adjusted by glycolic acid solution. Disodium EDTA is dissolved in a portion of water in a vessel with propeller stirrer. Amaze XT is sprinkled added into the agitated water and mixing without any lumps. This amaze XT mixture is slowly transferred into the main vessel and mixed slowly. Other ingredients are added one by one into the main vessel with slow mixing with similar intervals.

EXAMPLE-18

Manufacturing Process of Acne Control Face Scrub

TABLE 8

| Ingredients | % ingredients |
|---|---|
| Extract of *Aloe vera* | 0.05 |
| Extract of *Swietenia mahagoni* | 0.05 |
| Extract of *Salix tetrasperma* | 0.10 |
| Extract of *Curcuma longa* | 0.10 |
| Glycolic acid | 0.10 |
| Disodium EDTA | 0.05 |
| PEG-7 glyceryl cococate | 2.00 |
| Plantacare 2000 UP (Coco glucoside) | 10.00 |
| Amaze XT (Dehydro xanthangum) | 2.50 |
| Polyethylene Beads | 1.00 |
| Flora Beads | 0.25 |
| Glycacil 2000 (IPBC) | 0.30 |
| Neolone PE (MIC & Phenoxyethanol) | 0.60 |
| Perfume | 0.40 |
| DM Water | 82.50 |
| Total | 100.00 |

Manufacturing Method

A portion of water is taken in a vessel with propeller stirrer. EDTA DS is dissolved in the water. Carbomer is sprinkle into the water slowly. The propeller is allowed to stir till the carbomer becomes homogenous. The carbomer liquid is carefully neutralized by Triethanol amine with slow mixing. SLES is transferred into the main vessel with slow mixing; avoid excess foaming in the product. Other ingredients are added one by one to the product with slow mixing.

EXAMPLE-19

Manufacturing Process of Acne Control Pore Cleansing Face Mask

TABLE 9

| Name of ingredients | % Ingredients |
|---|---|
| Xanthan gum | 0.75 |
| Glycerin | 3.00 |
| Di sodium EDTA | 0.05 |
| Extract of *Aloe vera* | 0.25 |
| Extract of *Salix tetrasperma* | 0.05 |
| Extract of *Curcuma longa* | 0.10 |
| Extract of *Swietenia mahagonia* | 0.125 |
| Propylene glycol | 3.00 |
| Methyl paraben | 0.25 |
| Propyl paraben | 0.10 |
| Glycerin | 3.00 |
| Stearic acid | 2.00 |
| Ceto stearyl alcohol I.P | 0.50 |
| Iso propyl myristate B.P | 2.00 |
| Glyceryl mono state SE | 0.50 |
| Light Kaolin | 26.00 |
| Bentonite imp | 8.00 |
| Sodium lauryl sulfate | 0.20 |
| Imidazolidinyl urea | 0.20 |
| Fragrance | 0.50 |
| DM Water | 49.425 |
| Total | 100.00 |

Manufacturing Procedure

1. A Phase—Weigh Xanthan gum and Glycerine as per formula and disperse Xanthan gum in glycerine. Keep it at RT, Immediately transfer this to Phase B.
2. B Phase—Weigh DM water and EDTA in main Mixer and weigh extract of *Aloe vera* keep it separate.
3. C Phase—Weigh propylene glycol and extract of *Swietenia mahagoni* keep it separate.
4. D Phase—Weigh Methyl paraben and propyl paraben keep it separate.
5. E Phase—Weigh Stearic Acid, Ceto stearyl alcohol, Isopropyl myristate, Glyceryl mono stearate SE, extracts of *Salix tetrasperma* and *Curcuma longa* in the side kettle.
6. F Phase—Weigh Light Kaolin pure, Bentonite powder in a clean poly bag and mix well.
7. G Phase—Weigh SLS powder in a separate vessel & Imid urea in a separate vessel and dissolve in the water completely.
8. H Phase—Weigh perfume and keep it separate.

Manufacturing Process

1. Mix 'Phase B' ingredients in the main mixer filter through muslin cloth and add 'Phase A' to Phase B. Heat it to 80° C. and maintain the temperature.
2. Heat 'Phase C' ingredients to 80° C. in the melting kettle.
3. Transfer 'Phase C' into 'Phase A& B' in the main mixer at 80° C., mix for 10 minutes.
4. Add 'Phase D' slowly with continuous mixing to 'Phase ABC'. Mix 'Phase ABCD' till there is no lumps.

5. In oil phase kettle take all the Phase E ingredients melt it by heating to 80° C.
6. Transfer Phase E to Phase ABCD. Start Homogenize for 20 minutes.
7. To the above mixer add phase F ingredients slowly by continuously mixing, final product should be uniformly. Cool it.
8. At 55° C., Add 'Phase G' to the main mixer containing 'Phase ABCDEF' mixture and mix well.

The severity score for acne was analysed using Friedman test followed by Dunnett's multiple comparison posthoc test. The severity score was expressed as mean±SD. The minimum level of significance was fixed at $p<0.05$. Statistical analysis was carried out using GraphPad Prism software Version 4.01.

Results: The results and the statistical significance for various parameters employed during the Acne Control treatment are given in Table-10

TABLE 10

| | | Treatment Duration | | | | | |
|---|---|---|---|---|---|---|---|
| No. | Parameters | Initial | Day 14 | p value | Initial | Day 28 | p value |
| 1. | Open Comedones | 25 | 19 | p < 0.05 | 25 | 1 | p < 0.001 |
| 2. | Closed Comedones | 25 | 19 | p < 0.05 | 25 | 0 | p < 0.001 |
| 3. | Inflamed Papules | 20 | 7 | p < 0.05 | 20 | 0 | p < 0.001 |
| 4. | Pustules | 11 | 4 | NS | 11 | 1 | p < 0.05 |
| 5. | Blemishes | 18 | 15 | NS | 18 | 5 | p < 0.001 |
| 6. | Erythema | 16 | 8 | p < 0.05 | 16 | 3 | p < 0.001 |
| 7. | Hypopigmentation/ Hyperpigmentation | 13 | 4 | p < 0.05 | 13 | 3 | p < 0.05 |

Note:
NS: Not significant

9. Add 'Phase H' at 45° C. to the main mixer containing 'Phase ABCDEFG' and mix well.
10. Ensure the product is free of lumps. If required pass through colloidal mill.

EXAMPLE 20

Clinical Trial Evaluation of Acne-n-Pimple Total Care Package for the Treatment of *Acne-vulgaris*

An open Clinical trial on Acne Control was conducted in 25 patients with a mean age of 21.0±4.18 years with 9 of male and 16 female patients. The trial was aimed to evaluate the efficacy of Acne-n-Pimple total care package in *Acne-vulgaris*, which includes Anti-acne face wash, Anti-acne cream and anti-acne scrub.

Study Design: This was an open clinical trial. Twenty five patients satisfying the inclusion criteria were selected for the study after obtaining their informed consent. The volunteers were requested to use the acne package as per the direction of the investigator (Anti-acne face wash: twice a day, Anti-acne cream: twice daily on affected area after washing face with above face wash, Anti-acne-scrub: twice a week).

The patients were evaluated on Day 14 and on Day-28 of the study for black heads, inflamed papules, inflamed pustules, cysts, nodules, white heads and blemishes. The parameters were reviewed at initial and at the end of 14 and 28 days. At the end of the study, the results were statistically analyzed. Apart from above parameters the package was also evaluated for the cosmetic effect such as; exfoliation, moisturizing effect, smoothening effect, soothing effect and healing without scar formation etc.

The patients and the investigators were asked to rate the outcome of the treatment separately and the severity score was recorded and analyzed on all the days. The local/systemic adverse effects, if any, were noted during follow-up of the study.

Statistical analysis: Statistical analysis was carried out using Fischer's exact test to find out the level of significance.

The severity score for acne was 1.80±0.86, 1.32±0.90 and 0.00±0.00 initial, day 14 and on day 28, respectively. The improvement in severity score for acne on day 28 vs initial was significant at $p<0.001$ and day 28 vs day 14 was $p<0.01$ as compared to the initial values. The patient's remarks on the overall response to the treatment showed a complete cure in 84% and marked improvement in 8%. The investigators remarks on the overall response to the treatment showed a complete cure in 92% and marked improvement in 8%. Two patients developed signs of irritation and no adverse reactions were reported in all the remaining 23 patients. The test package was found to have good cosmetic acceptability and compliance of all the patients involved in the study.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. An herbal acne control composition comprising an extract of bark of *Salix tetrasperma*, a water extract of bark of *Swietenia mahagoni*, an extract of leaves of *Aloe vera*, an extract of rhizomes of *Curcuma longa* and pharmaceutically acceptable excipients, wherein said composition comprises stable and bioactive tetrahydrocurcuminoids, and wherein the extract of *Salix tetrasperma* comprises at least 8.9% by weight of salicylic acid.

2. The herbal acne control composition according to claim 1, wherein said extract of *Salix tetrasperma* is obtained by extracting *Salix tetrasperma* with a solvent or solvent system selected from the group consisting of organic solvents, water and a combination thereof.

3. The herbal acne control composition according to claim 1, wherein said extract of *Aloe vera* is obtained by extracting *Aloe vera* with a solvent or solvent system selected from the group consisting of organic solvents and water.

4. The herbal acne control composition according to claim 1, wherein said extract of *Curcuma longa* is obtained by extracting *Curcuma longa* with an organic solvent or solvent system selected from the group consisting of halogenated solvents, lower chain alcohol solvents and a combination thereof.

5. The herbal acne control composition according to claim 1, wherein said extracts of *Curcuma longa, Swietenia mahagoni, Salix tetrasperma* and *Aloe vera* are characterized by having rich content of bioactive constituents effective for anti-inflammatory, anti-bacterial, anti-kerolytic and anti-seborrhatic activities.

6. The herbal acne control composition according to claim 1, wherein said composition is effective for treating mild to severe pimples, black heads, white heads, papules, nodules, pustules, inflammatory lesions or cysts.

7. The composition according to claim 1, wherein the pharmaceutical excipients are selected from the group consisting of binder, diluent, surfactant, perfume, and preservative.

8. The herbal acne control composition according to claim 2, wherein said extract of *Salix tetrasperma* is obtained by extracting *Salix tetrasperma* with a solvent or solvent system selected from the group consisting of n-hexane, diethyl ether, dichloromethane, chloroform, ethyl acetate, acetone, methanol, ethanol and a combination thereof.

9. The herbal acne control composition according to claim 3, wherein said extract of *Aloe vera* is obtained by extracting *Aloe vera* with a solvent or solvent system selected from the group consisting of lower chain alcohol(s) and water.

10. The herbal acne control composition according to claim 3, wherein said extract of *Aloe vera* is obtained by extracting *Aloe vera* with a solvent or solvent system comprising methanol.

11. The herbal acne control composition according to claim 4, wherein said extract of *Curcuma longa* is obtained by extracting *Curcuma longa* with a solvent or solvent system selected from the group consisting of dichloromethane, methanol and a combination thereof.

12. The herbal acne control composition according to claim 1, wherein said composition is formulated in the form of cream, face wash, face gel, face scrub or face pack.

13. The herbal acne control composition according to claim 8, wherein said extract of *Salix tetrasperma* is obtained by extracting *Salix tetrasperma* with a solvent system consisting of n-hexane and acetone in a ratio of 1:1.

14. A process for preparing the herbal acne control composition of claim 1 comprising:
(i) extracting the bark of *Salix tetrasperma*, the leaves of *Aloe vera*, and the rhizomes of *Curcuma longa* with a solvent or solvent system, and extracting the bark of *Swietenia mahogoni* with water to form an extract;
(ii) filtering the resultant filtered extract;
(iii) concentrating the extract to dryness on a rotatory evaporator or on a steam bath at optimum temperature and;
(iv) producing the herbal acne control composition by mixing an effective concentration of said dried extract and pharmaceutically acceptable excipients.

15. The process according to claim 14, wherein said extractions are performed by percolation or hot-soxhlation.

16. The process according claim 14, wherein said solvent or solvent system for extracting *Salix tetrasperma* is selected from the group consisting of an organic solvent, water and a combination thereof.

17. The process according to claim 14, wherein said solvent or solvent system for extracting *Aloe vera* is selected from the group consisting of organic solvents and water.

18. The process according to claim 14, wherein said solvent or solvent system for extracting *Curcuma longa* is selected from the group consisting of halogenated solvents, lower chain alcohol solvents and a combination thereof.

19. The process according to claim 12, wherein the pharmaceutical excipients are selected from the group consisting of binder, diluent, surfactant, perfume, and preservative.

20. The process of claim 16, wherein said organic solvent is selected from the group consisting of a non-polar long chain hydrocarbon and an ester.

21. The process of claim 16, wherein said organic solvent is selected from the group consisting of n-hexane, ethyl acetate and a combination thereof.

22. The process of claim 17, wherein said solvent or solvent system is selected from the group consisting of lower chain alcohol(s) and water.

23. The process of claim 17, wherein said solvent or solvent system comprises methanol.

24. The process of claim 18, wherein said solvent or solvent system is selected from the group consisting of dichloromethane, methanol and a combination thereof.

25. The process of claim 16, wherein said solvent or solvent system is selected from the group consisting of n-hexane, acetone and a combination thereof.

26. The process of claim 25, wherein said combination consists of n-hexane and acetone in a ratio of 1:1.

* * * * *

UNITED STATES PATENT AND TRADEMARK OFFICE
CERTIFICATE OF CORRECTION

PATENT NO. : 7,785,638 B2  Page 1 of 1
APPLICATION NO. : 12/180279
DATED : August 31, 2010
INVENTOR(S) : Mitra et al.

It is certified that error appears in the above-identified patent and that said Letters Patent is hereby corrected as shown below:

On the title page, item [56] under "Other Publications," column 2, line 14, please delete "colorimetic" and insert therefore, --colorimetric--.
At column 1, line 12, please delete "Vera" and insert therefore, --vera--.
At column 3, line 60, please delete "FIG." and insert therefore, --FIGS.--.
At column 3, line 62, please delete "FIGS. 4. & 5." and insert therefore, --FIGS. 4 & 5.--.
At column 3, line 62, please delete "car" and insert therefore, --ear--.
At column 3, line 64, please delete "FIGS. 6. & 7." and insert therefore, --FIGS. 6 & 7.--.
At column 4, line 1, please delete "FIGS. 8. & 9." and insert therefore, --FIGS. 8 & 9.--.
At column 4, line 4, please delete "FIGS. 10. & 11." and insert therefore, --FIGS. 10 & 11.--.
At column 9, line 47, please delete "Inhibitor" and insert therefore, --Inhibitory--.
At column 18, line 6, in Claim 14, delete "*mahogoni*" and insert therefore, --*mahagoni*--.
At column 18, line 16, in Claim 16, after "according" insert --to--.
At column 18, line 27, in Claim 19, delete "claim 12," and insert therefore, --claim 14,--.

Signed and Sealed this
Nineteenth Day of April, 2011

David J. Kappos
*Director of the United States Patent and Trademark Office*